United States Patent [19]

Malpass et al.

[11] 4,263,217

[45] Apr. 21, 1981

[54] HYDROCARBON-SOLUBLE MAGNESIUM-ALUMINUM COMPOSITIONS

[75] Inventors: Dennis B. Malpass, LaPorte; Loyd W. Fannin, Dickinson, both of Tex.

[73] Assignee: Texas Alkyls, Inc., Deer Park, Tex.

[21] Appl. No.: 78,314

[22] Filed: Sep. 24, 1979

[51] Int. Cl.$^3$ ................................................ C07F 5/06
[52] U.S. Cl. ............................... 260/448 A; 252/182; 252/431 R
[58] Field of Search ................ 252/431 R; 260/448 A

[56] References Cited

U.S. PATENT DOCUMENTS

| | | | |
|---|---|---|---|
| 3,149,136 | 9/1964 | Bruce et al. | 260/448 A |
| 3,737,393 | 6/1973 | de Vries | 252/431 R |
| 3,910,979 | 10/1975 | Eidt | 260/448 A |
| 4,128,501 | 12/1978 | Smith et al. | 252/431 R |
| 4,135,046 | 1/1979 | Harris et al. | 252/431 R X |
| 4,155,926 | 5/1979 | Eidt | 260/448 A |
| 4,170,603 | 10/1979 | Fannin | 252/431 R X |
| 4,172,050 | 10/1979 | Gessell | 252/431 R |

FOREIGN PATENT DOCUMENTS 977766 11/1975 Canada ................................ 260/448 A

*Primary Examiner*—Helen M. S. Sneed
*Attorney, Agent, or Firm*—M. Henry Heines

[57] ABSTRACT

A composition of matter is disclosed comprising a dialkylmagnesium compound of the formula RMgR' in which R and R' are straight-chain alkyl groups of 1 to 4 carbon atoms each, either identical in length or differing by one carbon atom, and an aluminum diene polymer. The composition is soluble in aliphatic, cycloaliphatic, and aromatic hyrocarbon solvents.

6 Claims, No Drawings

HYDROCARBON-SOLUBLE MAGNESIUM-ALUMINUM COMPOSITIONS

BACKGROUND OF THE INVENTION

Diorganomagnesium compounds are well known for their usefulness in a wide variety of chemical reactions. As reagents, these compounds can be used for the reduction of ketones, the metalation of aromatic compounds and the alkylation of metal halides or oxides to the corresponding metal alkyls. While they perform many of the same types of functions performed by Grignard reagents, diorganomagnesium compounds, owing to differences in electronic and steric factors, are more reactive than Grignard reagents towards certain types of compounds. Some of their uses are disclosed in Kamienski et al., U.S. Pat. No. 3,646,231, Feb. 29, 1972, and Kamienski et al., U.S. Pat. No. 3,822,219, July 2, 1974. As catalysts, diorganomagnesium compounds are useful in the dimerization and polymerization of olefins (Stamicarbon, British Pat. No. 1,251,177, Oct. 27, 1971), the polymerization of epoxides (Ito et al., U.S. Pat. No. 3,444,102, May 13, 1969), and the preparation of telomers (Kamienski et al., U.S. Pat. No. 3,742,077, June 26, 1973).

The utility of diorganomagnesium compounds is lessened by the fact that many are either solids or highly viscous liquids and all are unstable upon exposure to moisture and air. This problem is generally overcome either by dissolving the compound in an inert hydrocarbon solvent or by solvating the compound and keeping it under an inert atmosphere. Many diorganomagnesium compounds, particularly those with straight-chain lower alkyl groups with a chain length of up to 4 carbon atoms, are insoluble by themselves in hydrocarbon solvents and thus require solubilizing agents which will form a soluble complex. Examples of such solubilizing agents are alkyllithium compounds (Kamienski et al., U.S. Pat. No. 3,742,077, June 26, 1973), dialkyl zinc compounds (Ito et al., U.S. Pat. No. 3,444,102, May 13, 1969), alkali metal hydrides (Ashby, U.S. Pat. No. 3,655,790, Apr. 11, 1972), and organoaluminum compounds (deVries, U.S. Pat. No. 3,737,393, June 5, 1973, and Kobetz et al., U.S. Pat. No. 3,028,319, Apr. 3, 1962).

Solvation involves the use of an ether or an organic base molecule in direct association with the magnesium atom. Although the resulting complex is liquid in form, it is unfavorable in terms of reactivity, since the ether or base molecule inhibits the effectiveness of the organomagnesium compound, particularly when the latter is used as a Ziegler-type catalyst. The use of ether is particularly undesirable due to considerations of flammability and explosibility, and because it introduces soluble alkyl magnesium halide according to the equilibrium of Schlenk, *Berichte der Deutschen Chemischen Gesselschaft*, Vol. 64, p. 734 (1931), by promoting the reaction $$R_2Mg + MgX_2 \rightleftharpoons 2RMgX$$

where R is alkyl and X is halogen.

Solubilization also serves to enhance the reaction rate and facilitate handling and transferring by reducing the viscosity of reaction mixtures. Although similar results have been achieved by the use of chloroaryl solvents to form low viscosity suspensions of the insoluble compounds, as described in Nudenberg et al., U.S. Pat. No. 3,264,360, Aug. 2, 1966, the results are more effective with a homogeneous mixture.

Solubilization also facilitates the preparation of organomagnesium compounds, since those which are insoluble are difficult to prepare in a form free of undesirable halides. The preparation of soluble organomagnesium compounds by direct reaction of magnesium metal with an alkyl halide is disclosed in Glaze and Selman, *Journal of Organometallic Chemistry*, Vol. 5, p. 477 (1967), and W. N. Smith, *Journal of Organometallic Chemistry*, Vol. 64, p. 25 (1974), where the alkyl halide contains a minimum of 5 carbon atoms. Since the products made from such starting materials are inherently hydrocarbon-soluble, they are readily separable from the concurrently produced magnesium halide and whatever unreacted magnesium remains. When straight-chain alkyls of less than 5 carbon atoms in length are used, however, the product remains as a solid in the slurry formed by the solvent, the magnesium halide, and the unreacted magnesium, since the product itself is insoluble in the solvent. This process thus requires a solubilizing agent to make recovery of the product possible when lower alkyl halides are used. Lower alkyl organomagnesium compounds are particularly desirable as reagents and catalysts owing to their relatively high magnesium content on a weight basis.

Other methods of preparation include the mercury-magnesium exchange method, as disclosed in Cowan and Mosher, Journal of Organic Chemistry, Vol. 27, p. 1 (1962), and the dioxanate-precipitation method as disclosed in Schlenk, supra. The mercury method, $$R_2Hg + Mg \rightarrow R_2Mg + Hg$$

where R is alkyl, is limited by the high cost of dialkylmercury compounds, and the health hazards involved in their use. The reaction itself is hazardous since it proceeds rapidly and exothermically after an inhibition period.

The dioxanate-precipitation method, $$2RMgX + C_4H_8O_2 \xrightarrow{ether} R_2Mg + C_4H_8O_2 \cdot MgX_2 \downarrow$$

where R is alkyl and X is halogen, involves removal of magnesium halide from ether solutions of Grignard reagents by precipitation of a complex which the dioxane forms with the halide. This is a tedious process and results in an etherated dialkylmagnesium complex from which the ether must be removed prior to use of the dialkylmagnesium as a catalyst.

Dialkylmagnesiums can also be prepared from alkyllithiums, as described in Kamienski et al., U.S. Pat. No. 3,646,231, Feb. 29, 1972, by precipitation of lithium halide, $$MgX_2 + 2RLi \rightarrow R_2Mg + 2LiX$$

where R is alkyl and X is halogen. As in the Glaze and Selman method described above, this process is unsuitable for straight-chain lower alkyl diorganomagnesiums which are insoluble in hydrocarbon solvents, since separation of the diorganomagnesium from the product mixture is impossible. The use of basic solvents renders separation possible but requires subsequent desolvation.

It is therefore an object of the present invention to provide a hydrocarbon-soluble diorganomagnesium composition of high magnesium content.

A further object of the present invention is to provide a process by which hydrocarbon-soluble diorganomagnesium compositions of high magnesium content can be prepared by the direct reaction of alkyl halides with magnesium.

A still further object of the present invention is to provide a means for solubilizing straight-chain lower alkyl diorganomagnesium compounds in hydrocarbon solvents.

Further objects will be apparent from the following description.

BRIEF DESCRIPTION OF THE INVENTION

It has now been discovered that complexes comprising a normally insoluble dialkylmagnesium compound and an aluminum diene polymer are both stable and soluble in hydrocarbon solvents.

Dialkylmagnesium compounds which are normally insoluble in hydrocarbon solvents are those having the formula $$RMgR'$$

in which R and R' are straight-chain alkyl groups of 1 to 4 carbon atoms each, either identical in length or differing by one carbon atom. Examples are dimethylmagnesium, diethylmagnesium, di-n-propylmagnesium, di-n-butylmagnesium, methylethylmagnesium, ethyl-n-propylmagnesium, and n-propyl-n-butylmagnesium.

The aluminum diene polymers contemplated for use in the present invention are those having the formula

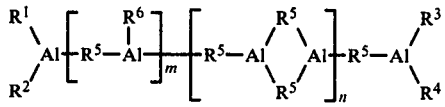

in which $R^1$, $R^2$, $R^3$, and $R^4$ are independently selected from the group consisting of the isobutyl radical, an alkenyl radical of said diene, an alkenyl radical formed by the addition of said diene to the isobutyl radical, and an alkadienyl radical formed by the addition of said diene to an alkenyl radical of said diene, or either or both of the pairs $R^1R^2$ and $R^3R^4$ conjointly form an alkylene radical;

$R^5$ is selected from the group consisting of an alkylene radical of said diene, an alkylene radical formed from the addition product of said diene with said isobutyl radical, and an alkenylene radical formed from the addition product of said diene with the alkylene radical of said diene;

$R^6$ is selected from the group consisting of the $R^1$ radical and radicals having the formula

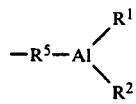

m is an integer from 0 to 10; and
n is an integer from 0 to 10.
Preferred substituents are as follows:

$R^1$, $R^2$, $R^3$, and $R^4$ are preferably independently selected from the group consisting of the isobutyl radical and an alkenyl radical of the diene, or either or both of the pairs $R^1R^2$ and $R^3R^4$ conjointly form an alkylene radical;

$R^5$ is preferably an alkylene radical of the diene; and m and n are each preferably 0 to 5, most preferably 0 to 2.

The term "diene" is intended to include both straight- and branched-chain hydrocarbons containing 4 to 12, preferably 4 to 6 carbon atoms and at least two double bonds located at terminal positions on the chains or any of the branches. Thus, trienes such as myrcene are included in this definition, as well as compounds with more than three double bonds. Preferably, the "diene" contains only two double bonds. Examples include isoprene and 1,3-butadiene.

The term "alkylene" is used herein to denote a bivalent saturated hydrocarbon radical, which may be a straight chain or a branched chain. Examples include such radicals as —CH$_2$CH$_2$CH$_2$—, —CH$_2$CH$_2$CH$_2$CH$_2$—, and —CH$_2$CH(CH$_3$)CH$_2$CH$_2$—. Preferably, the alkylene radicals formed by $R^1R^2$ and $R^3R^4$ contain 4 to 7 carbon atoms each.

The term "alkenylene" is used herein to denote a bivalent unsaturated hydrocarbon radical containing one double bond. The alkenylene radical may form either a straight chain or a branched chain. Examples include such radicals as —CH=CHCH$_2$CH$_2$—, —CH=CHCH(CH$_3$)CH$_2$—, and —CH=C(CH$_3$)CH$_2$CH$_2$—. Preferred alkenylene radicals contain 4 to 7 carbon atoms each.

The relative quantities of the dialkylmagnesium compound and aluminum diene polymer are such that the atomic ratio of magnesium to aluminum is from about 0.1 to about 5.0, preferably from about 1.0 to about 5.0, most preferably from about 1.0 to about 3.0. The lower limit of these ranges is much less critical than the upper limit, since the aluminum polymer is soluble by itself. Mg/Al ratios toward the upper limits of these ranges are preferred in the interest of maximizing the magnesium utility.

All carbon atom ranges and integer ranges stated herein are intended to be inclusive of their upper and lower limits.

The concept embodied in rendering soluble an otherwise insoluble compound is often more accurately expressed as causing a substantial increase in the solubility of a compound of extremely low solubility. The present invention is intended to encompass this concept, and is stated in absolute rather than relative terms for convenience only.

DETAILED DESCRIPTION OF THE INVENTION

To form the complexes of the present invention, the dialkylmagnesium compound in solid form and the polymer, which is normally in liquid form, can be physically combined in the hydrocarbon solvent. Solubilization can be hastened by heating the resulting mixture to a temperature of about 50° C. or higher. The rate of solubilization increases as the temperature is raised. A clear solution results which is readily separable from any insolubles retained with the compounds. Once the compounds are dissolved, they will remain in solution upon any subsequent lowering of temperature.

If desired, separation of the solution from the remaining undissolved solids can be enhanced by the use of viscosity reducing agents of which a wide variety are known in the art. Organoaluminum compounds are particularly useful in this regard. Trialkylaluminums, dialkylaluminum halides, and alkylaluminum dihalides are examples. These compounds can be added directly or generated in situ from aluminum chloride. Aluminum alkoxides, bis-oxides, and hydrides are also effective.

Alternatively, the dialkylmagnesium compound can be prepared directly in the same solvent in which the complex is to be dissolved, and the polymer added either prior to or immediately following the reaction. Any preparation technique is suitable in which neither the by-products nor the unreacted starting materials are soluble in the final mixture. The insolubles can thus be easily filtered off. One such technique involves the direct reaction between metallic magnesium and the appropriate alkyl halide, or two alkyl halides in succession, if two different alkyl groups are desired. The concurrently produced magnesium chloride forms a precipitate which is readily removed from the solution together with any unreacted magnesium still present, after the aluminum polymer has been added and the dialkylmagnesium compound is thus solubilized. Another technique involves the use of a Grignard reagent, preferably freed of all ether used in its preparation. The desired solution is obtained by combining the desolvated Grignard reagent with the aluminum diene polymer in the solvent. The polymer dissolves only the dialkylmagnesium compound.

When magnesium is reacted directly with an alkyl halide, commercial grade magnesium turnings or shavings can be used. It is preferable, however, to use higher surface area forms of the metal. While the surface area can be increased by milling, the use of finely divided magnesium powder is most preferred, with a particle size equal to or less than about 150 microns. This form of the metal serves to enhance the reaction rate and minimize the occurrence of Wurtz coupling reactions.

When methyl or ethyl halides are used, the reaction rate is so slow at the temperatures at which such reactions are normally run that extra heat or a magnesium activating agent are normally used to initiate the reaction. The term "magnesium activating agent" is used herein to denote any substance which, when contacted with magnesium, will cause the reaction to occur at a substantially faster rate. Many activating agents are known in the art. Typical examples are $AlCl_3$, $AlCl_3$-ether complexes, N,N-dimethylaniline, molecular iodine, alkyl halides of at least three carbon atoms, Grignard reagents, and hydrocarbon-soluble dialkylmagnesium compounds. When heating is used as a reaction initiator, the temperature is raised to between about 125° C. and about 350° C., preferably from about 150° C. to about 250° C., and most preferably from about 150° C. to about 200° C., for a short period of time until the reaction has begun. Once the reaction is initiated, the temperature can be lowered for the remainder of the reaction. Although the reaction can occur over a wide temperature range once the magnesium is activated, it will be most convenient to operate between about 20° C. and about 200° C., preferably between about 50° C. and about 175° C., and most preferably between about 100° C. and about 150° C. At least 10% by weight of alkyl halide based on the weight of magnesium metal must be present during thermal activation.

The temperature ranges quoted above are not critical. For the most part, they are subject only to practical considerations. The minimum temperature is dictated largely by process economics, while the maximum temperature is limited only by the possibility of alkyl halide decomposition and consideration of energy conservation.

The term "halide" as used herein denotes chloride, bromide, or iodide, or combinations thereof. Chlorides are generally preferred for reasons of economy. Usually, a small amount of halide is present in the final product solution. This can be minimized by the use of chlorides rather than iodides or bromides, since the amount of soluble halide observed decreases in the order $I > Br > Cl$.

The reactant mole ratio can be varied over a wide range. No particular range is critical to the performance of any of the reactions. Normally, however, the starting materials will be such that the mole ratio of magnesium to total halides is from about 1.0 to about 2.0, preferably from about 1.1 to about 1.3. The excess magnesium inherent in mole ratios greater than 1.0 is effective in minimizing Wurtz coupling reactions.

The term "hydrocarbon solvent" is used herein to designate aliphatic, cycloaliphatic, and aromatic hydrocarbons. Illustrative of aliphatic solvents are n-pentane, iso-pentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylene, ethylbenzene, tetralin, and α-methylnaphthalene. Preferred solvents are those containing 5 to 20 carbon atoms, inclusive. More preferred are those containing 6 to 15 carbon atoms, inclusive. Particularly preferred solvents are those which have boiling points between about 69° C. and about 110° C.

The concentration of dialkylmagnesium in the solvent is not critical and the compounds are soluble over a wide range of concentration. The solution viscosity increases with concentration, however. Therefore, the preferred dialkylmagnesium concentration is from about 0.2 to about 12.0 weight percent, most preferably from about 1.0 to about 5.0 weight percent in terms of magnesium.

The hydrocarbon solvent may be added before, during, or after the reaction. It will be most convenient to add the solvent prior to or during the reaction, so that further reaction is not inhibited by high viscosity.

Magnesium alkyls are pyrophoric substances, capable of spontaneous ignition upon contact with air. To prevent such ignition, and also to prevent oxidation of the metallic magnesium, the reactions must be carried out in the absence of more than trace amounts of oxygen. Thus, the reaction is normally carried out in an atmosphere of inert gas such as nitrogen or argon, or in an atmosphere of the alkyl halide gas used in the reaction. The reaction must also be conducted in the substantial absence of water, due to the susceptibility of the system components to decomposition in the presence of water.

The aluminum diene polymer can be prepared by a variety of techniques, such as the reaction of an alkenyl halide with an aluminum-magnesium alloy, the reaction of an aluminum hydride or a lithium aluminum hydride with a diolefin, or the reaction of finely divided aluminum with hydrogen and a diolefin in the presence of an aluminum trialkyl. The preferred method is the addition or hydroalumination reaction between the desired diolefin and triisobutylaluminum or diisobutylaluminum hydride. Each of these preparation techniques is described in Bruce et al., U.S. Pat. No. 3,149,136, Sept. 15, 1964, with particular emphasis on the addition reaction.

Once the R₂Mg/(aluminum diene polymer) complex is formed in hydrocarbon solution, the solids can be removed by any conventional technique, for example: centifuging, decanting, filtration, etc. The resulting solution can then be diluted or evaporated to achieve the desired concentration.

The invention is illustrated by the following examples.

EXAMPLE 1

Solubilization of Diethylmagnesium

A 12-ounce glass pressure bottle immersed in an oil heat bath and equipped with a thermowell, variable diptube, and magnetic stirring bar was purged with nitrogen and charged with 20.0 g (0.822 g-atom) of a 100-mesh magnesium powder, 167 g of n-heptane, and 1.0 ml of a 10 weight % solution of n-butylethylmagnesium in n-heptane as a magnesium activating agent. The mixture was heated to 120° C. and the reactor bottle was pressurized slightly with ethyl chloride gas from a nitrogen-pressurized cylinder. After an initial temperature rise was observed, more ethyl chloride was fed to the reactor bottle until a total of 43.7 g (0.677 mole) of ethyl chloride had been added and the pressure inside the bottle had reached 64 pounds per square inch absolute (44 newtons per square centimeter absolute). The bottle was then cooled and vented to the atmosphere. After the solids had settled, a 14.2 g sample of the liquid phase was removed and analyzed, the results indicating 0.09 weight % chloride in soluble form and no detectable magnesium.

At this point, a commercially available aluminum diene polymer commonly known as "isoprenylaluminum" was added to the reaction slurry. The polymer, obtained from Stauffer Chemical Company, Specialty Chemical Division, Westport, Connecticut, is manufactured from triisobutylaluminum and isoprene, contains about 15% aluminum by weight, with an average structure containing approximately two isoprene-derived units for every isobutyl unit, and has an average molecular weight of 400 (according to a cryoscopic determination in cyclohexane).

The quantity of isoprenylaluminum initially added was 11.2 g, corresponding to 0.062 g-atom of aluminum. The slurry was then heated to 120° C. for about two hours, and a 25.4 g sample of the liquid phase was removed for analysis. The analytical results indicated that the liquid solution contained 1.77 weight % magnesium and 0.87 weight % aluminum, or a Mg/Al atomic ratio of 2.26.

A further 11.2 g (0.062 g-atom Al) portion of isoprenylaluminum was then added to the slurry, followed by additional heating. Analysis of the resulting liquid phase then showed 3.51% magnesium and 2.61% aluminum, or a Mg/Al ratio of 1.49.

EXAMPLE 2

Solubilization of Di-n-butylmagnesium

A 500-ml flask equipped with a reflux condenser, addition funnel, thermowell, and magnetic stirring bar was purged with nitrogen and charged with 12.5 (0.518 g-atom) of 100-mesh magnesium powder. Approximately 1.0 ml of n-butyl chloride was then added while the temperature was closely monitored to observe reaction initiation. After a temperature increase was observed, 190 g of n-heptane was added, and additional n-butyl chloride was fed at a rate just sufficient to maintain reflux temperature. The n-butyl chloride feed was discontinued after a total of 45.2 g (0.488 mole) had been added, although reflux was continued for an additional hour. The reaction vessel and contents were then cooled, and a 110-g portion of the slurry was transferred to a nitrogen-filled sample bottle sealed with a septum.

The same type of polymer used in Example 1 was then added in a quantity of 1.2 g, or 0.007 g-atom in terms of aluminum content, and the slurry was heated in an oil bath at 65° C. for one hour. The liquid phase was then sampled and analyzed to indicate 1.15% magnesium and 0.28% aluminum, or a Mg/Al ratio of 4.56.

A further 6.1 g (0.034 g-atom Al) portion of polymer was added, followed by further heating. Analysis of the resulting liquid phase then indicated 1.54% magnesium and 1.35% aluminum, or a Mg/Al ratio of 1.28.

What is claimed is:

1. A hydrocarbon-soluble complex comprising
   (a) a dialkylmagnesium compound of the formula RMgR' in which R and R' are straight-chain alkyl groups of 1 to 4 carbon atoms each, and either have identical lengths or differ from each other in length by one carbon atom, and
   (b) an aluminum diene polymer of the formula

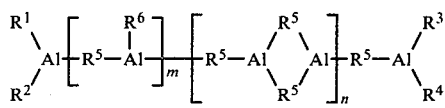

in which
   $R^1$, $R^2$, $R^3$, and $R^4$ are independently selected from the group consisting of the isobutyl radical, an alkenyl radical of said diene, an alkenyl radical formed by the addition of said diene to the isobutyl radical, and an alkadienyl radical formed by the addition of said diene to an alkenyl radical of said diene, or
   either or both of the pairs $R^1R^2$ and $R^3R^4$ conjointly form an alkylene radical of 4 to 7 carbon atoms;
   $R^5$ is selected from the group consisting of an alkylene radical of said diene, an alkylene radical formed from the addition product of said diene with said isobutyl radical, and an alkenylene radical formed from the addition of said diene with the alkylene radical of said diene;
   $R^6$ is selected from the group consisting of the $R^1$ radical and radicals having the formula

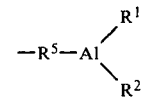

m is an integer from 0 tl 2, and
   n is an integer from 0 to 2,
   said diene being either isoprene or 1,3-butadiene, such that the atomic ratio of magnesium to aluminum is from about 0.1 to about 5.0.

2. A complex according to claim 1 in which the diene is isoprene.

3. A complex according to claim 1 in which $R^1$, $R^2$, $R^3$, and $R^4$ are independently selected from the group consisting of the isobutyl radical and an alkenyl radical of the diene.

4. A complex according to claim 1 in which $R^5$ is an alkylene radical of the diene.

5. A complex according to claim 1 in which the atomic ratio of magnesium to aluminum is from about 1.0 to about 5.0.

6. A complex according to claim 1 in which the atomic ratio of magnesium to aluminum is from about 1.0 to about 3.0.

* * * * *